US00PP17925P2

(12) United States Plant Patent
Nobbmann

(10) Patent No.: US PP17,925 P2
(45) Date of Patent: Aug. 14, 2007

(54) ***LAMIUM* PLANT NAMED 'CHECKIN'**

(50) Latin Name: *Lamium maculatum*
Varietal Denomination: Checkin

(76) Inventor: Lüder Nobbmann, Weidenhäuser Str. 45, D-35625 Hüttenberg (DE)

( * ) Notice: Subject to any disclaimer, the term of this patent is extended or adjusted under 35 U.S.C. 154(b) by 0 days.

(21) Appl. No.: 11/349,689

(22) Filed: Feb. 7, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
(74) *Attorney, Agent, or Firm*—C. A. Whealy

(57) ABSTRACT

A new and distinct cultivar of *Lamium* plant named 'Checkin' characterized by its upright, outwardly spreading and mounded plant form; freely branching habit; dense and bushy growth habit; unique and attractive silver and green bi-colored variegated foliage; freely and continuous flowering habit; light pink-colored flowers; and relative tolerance to leaf spot pathogens.

1 Drawing Sheet

Figure 1:
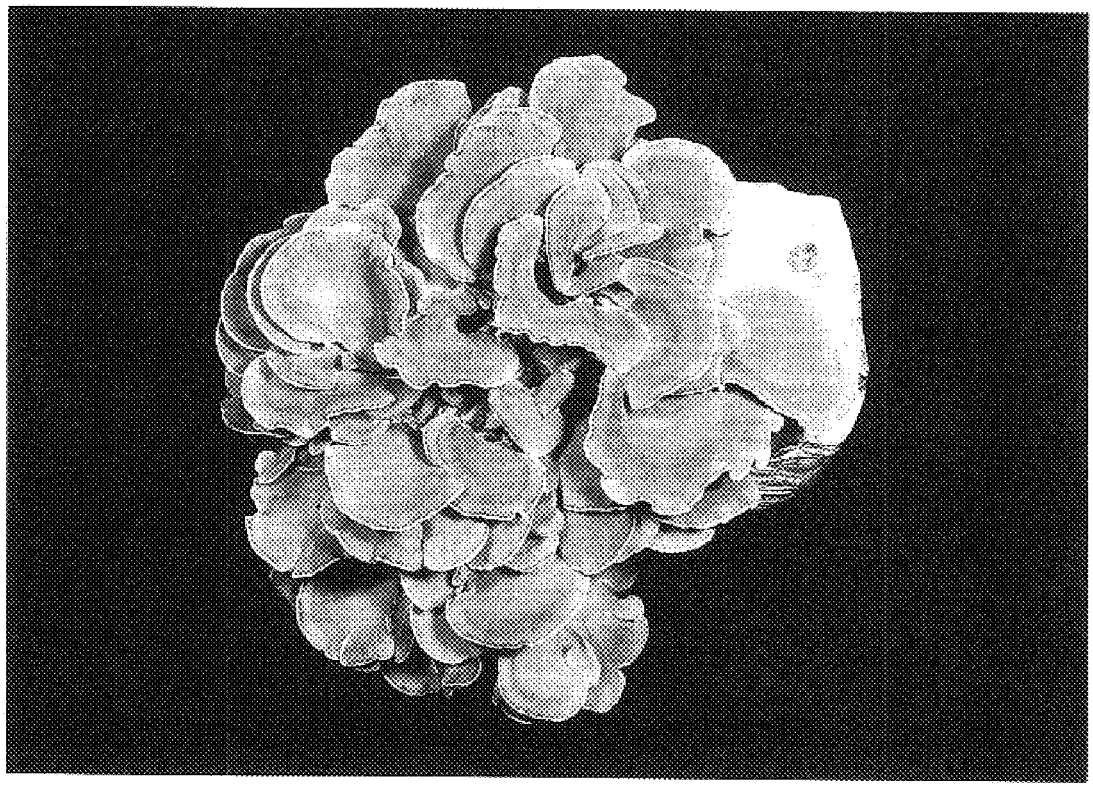

Botanical designation: *Lamium maculatum.*
Cultivar denomination: 'Checkin'.

BACKGROUND OF THE INVENTION

The present invention relates to a new and distinct cultivar of *Lamium* plant, botanically known as *Lamium maculatum* and referred to by the name 'Checkin'.

The new *Lamium* originated from an open-pollination during the summer of 2000 of the *Lamium maculatum* cultivar Chequers, not patented, as the female, or seed, parent with an unidentified seedling selection of *Lamium maculatum,* as the male, or pollen, parent. The cultivar Checkin was discovered and selected by the Inventor as a flowering plant within the progeny from the aforementioned open-pollination in a controlled environment in Hüttenberg, Germany during the summer of 2001.

Asexual reproduction of the new *Lamium* by terminal cuttings in a controlled environment in Hüttenberg, Germany since 2001, has shown that the unique features of this new *Lamium* are stable and are reproduced true to type in successive generations.

SUMMARY OF THE INVENTION

The new *Lamium* has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Checkin' and distinguish 'Checkin' as a new and distinct cultivar:

1. Upright, outwardly spreading and mounded plant form.
2. Freely branching habit; dense and bushy growth habit.
3. Unique and attractive silver and green bi-colored variegated foliage.
4. Freely and continuous flowering habit.
5. Light pink-colored flowers.
6. Relatively tolerant to leaf spot pathogens.

Plants of the new *Lamium* differ from plants of the female parent, the cultivar Chequers, in the following characteristics:

1. Plants of the new *Lamium* have larger leaves than plants of the cultivar Chequers.
2. Plants of the new *Lamium* and the cultivar Chequers differ in leaf and flower coloration.

Plants of the new *Lamium* can be compared to plants of the cultivar White Nancy, not patented. In side-by-side comparisons, plants of the new *Lamium* differed from plants of the cultivar White Nancy in the following characteristics:

1. Plants of the new *Lamium* and the cultivar White Nancy differed in leaf coloration.
2. Plants of the new *Lamium* had pink-colored flowers whereas plants of the cultivar White Nancy had white-colored flowers.

Plants of the new *Lamium* can be compared to plants of the cultivar Orchid Lace, not patented. In side-by-side comparisons, plants of the new *Lamium* differed from plants of the cultivar Orchid Lace in the following characteristics:

1. Plants of the new *Lamium* and the cultivar Orchid Lace differed in leaf coloration.
2. Plants of the new *Lamium* had pink-colored flowers whereas plants of the cultivar Orchid Lace had dark lilac-colored flowers.

BRIEF DESCRIPTION OF THE PHOTOGRAPHS

The accompanying colored photographs illustrate the overall appearance of the new *Lamium,* showing the colors as true as it is reasonably possible to obtain in colored reproductions of this type.

The photograph at the bottom of the sheet comprises a side perspective view of a typical plant of 'Checkin' grown in a container.

The photograph at the bottom of the sheet comprises a close-up view of typical developing flowers and open flowers of 'Checkin'.

DETAILED BOTANICAL DESCRIPTION

The aforementioned photographs and following observations and measurements describe plants grown in Bonsall, Calif., in an outdoor nursery during the summer with day temperatures ranging from 18° C. to 35° C. and night temperatures ranging from 13° C. to 18° C. Plants were grown in 15-cm containers and were about three months old. Color references are made to The Royal Horticultural Society Colour Chart, 1995 Edition, except where general terms of ordinary dictionary significance are used.

Botanical classification: *Lamium maculatum* cultivar Checkin.

Parentage:

*Female, or seed, parent.*—*Lamium maculatum* cultivar Chequers, not patented.

*Male, or pollen, parent.*—An unidentified seedling selection of *Lamium maculatum,* not patented.

Propagation:

*Type.*—By cuttings.

*Time to initiate roots, summer.*—About 15 days at 22° C.

*Time to initiate roots, winter.*—About 18 days at 22° C.

*Time to develop roots, summer.*—About 18 days at 22° C.

*Time to develop roots, winter.*—About 22 days at 22° C.

*Root description.*—Fine, fibrous; white in color.

*Rooting habit.*—Freely branching; dense.

Plant description:

*General appearance.*—Herbaceous; upright, outwardly spreading and mounded plant form; silver and green bi-colored foliage; numerous pink-colored flowers.

*Plant height.*—About 16 cm.

*Plant diameter or spread.*—About 32 cm.

*Growth rate/vigor.*—Moderately vigorous.

*Lateral branch description.*—Branching habit: Freely branching habit, typically about six primary lateral branches each with numerous secondary laterals. Length: About 16 cm. Diameter: About 2.5 mm. Internode length: About 7 cm to 10 cm. Texture: Pubescent. Color: 144A.

*Foliage description.*—Arrangement: Opposite, simple. Shape: Broadly deltoid. Apex: Rounded. Base: Cordate; shallow. Margin: Crenate. Length: About 3.7 cm. Width: About 4 cm. Texture, upper and lower surfaces: Pubescent. Venation pattern: Pinnate; reticulate. Petiole length: About 7 mm. Petiole diameter: About 1 mm. Petiole texture, upper and lower surfaces: Pubescent. Color: Developing leaves, upper surface: 147A. Developing leaves, lower surface: 147B. Fully expanded leaves, upper surface: Ground color, 147A; irregularly shaped central patches, 147A overlain with 195B to 195C; venation, 147B. Fully expanded leaves, lower surface: 147B; venation, 147C. Petiole, upper and lower surfaces: 144B.

Flowering description:

*Flowers.*—Zygomorphic axillary single flowers arranged in verticillasters. Five modified petals fused into bilabiate mint flower form with bi-lobed galeate upper lip and three-lobed lower lip. Flowers sessile. Flowers not persistent. Flowers not fragrant.

*Natural flowering season.*—Plants flower from spring to fall in Southern California; flowering continuous during this period. Individual flowers last about five to seven days on the plant.

*Quantity of flowers.*—Freely flowering habit with typically about 48 open flowers and flower buds per flowering stem; potentially about 500 flowers per plant.

*Flower length.*—About 2.4 cm.

*Flower width, upper galea petal.*—About 8 mm.

*Flower width, mid-section.*—About 6 mm.

*Flower tube diameter.*—About 2 mm.

*Flower depth.*—About 1.2 cm.

*Flower buds.*—Shape: Obovate. Length: About 1.2 cm. Diameter: About 4 mm. Color: 196C.

*Petals.*—Shape, galeate upper lip: Bi-lobed; rounded with emarginate apex; base, fused. Shape, lower lip: Three-lobed; elongated with rounded and ragged apex; base, fused. Length, upper lip: About 8 mm. Length, lower lip: About 6 mm. Width, upper lip: About 8 mm. Width, lower lip: About 4 mm. Texture, upper lip, upper and lower surfaces: Pubescent. Texture, lower lip, upper and lower surfaces: Smooth, glabrous. Color: When opening, upper surface: 75C to 75D. When opening, lower surface: 76B. Fully opened, upper surface: 75A; color becoming closer to 76C with development. Fully opened, lower surface: 75B to 75C; base of tube, 196D.

*Sepals.*—Quantity: Five sepals fused at the base; five-pointed, star-shaped calyx. Apex: Acuminate to apiculate. Margin: Entire. Length: About 5 mm. Width: About 2 mm. Texture, upper and lower surfaces: Pubescent. Color, upper and lower surfaces: 146A.

*Androecium.*—Stamen number: Typically four per flower. Anther shape: Ovate. Anther length: Less than 1 mm. Anther color: 25C. Amount of pollen: Scarce. Pollen color: 25A.

*Gynoecium.*—Pistil number: One per flower. Pistil length: About 1.2 cm. Style length: About 9 mm. Style color: 76D. Stigma shape: Bi-parted. Stigma color: 76D. Ovary color: 144B.

*Seed/fruit.*—Seed and fruit production have not been observed.

Disease resistance: Plants of the new *Lamium* have been observed to be relatively resistant to leaf spot diseases common to *Lamium.* Plants of the new *Lamium* have not been observed to be resistant to pests and other pathogens of *Lamium.*

Temperature tolerance: Plants of the new *Lamium* have been observed to tolerate temperatures from about −20° C. to about 35° C.

It is claimed:

1. A new and distinct cultivar of *Lamium* plant named 'Checkin' as illustrated and described.

* * * * *